US008394592B2

(12) United States Patent
El-Zein et al.

(10) Patent No.: US 8,394,592 B2
(45) Date of Patent: Mar. 12, 2013

(54) METHODS FOR ASSESSING CANCER SUSCEPTIBILITY TO CARCINOGENS IN TOBACCO PRODUCTS

(75) Inventors: Randa A. El-Zein, League City, TX (US); Matthew B. Schabath, Houston, TX (US); Carol J. Etzel, Houston, TX (US); Mirtha S. Lopez, Porter, TX (US); Margaret R. Spitz, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 699 days.

(21) Appl. No.: 12/304,298

(22) PCT Filed: Jun. 11, 2007

(86) PCT No.: PCT/US2007/070891
§ 371 (c)(1),
(2), (4) Date: Jan. 15, 2010

(87) PCT Pub. No.: WO2007/146883
PCT Pub. Date: Dec. 21, 2007

(65) Prior Publication Data
US 2010/0173289 A1    Jul. 8, 2010

Related U.S. Application Data

(60) Provisional application No. 60/804,532, filed on Jun. 12, 2006.

(51) Int. Cl.
*C12Q 1/68* (2006.01)
*C12Q 1/00* (2006.01)
*G01N 1/30* (2006.01)
*G01N 33/48* (2006.01)

(52) U.S. Cl. ........... 435/6.14; 435/4; 435/6.1; 435/6.11; 435/40.5; 436/63; 436/64

(58) Field of Classification Search ........................ None
See application file for complete search history.

(56) References Cited

PUBLICATIONS

El-Zein et al (Proc Amer Assoc Cancer Research. Abstracts Online. 2006. 47. Abstract #451; posted online and mailed Mar. 3, 2006.*
Cheng et al. Mutation Research. 1996. 349: 43-50.*
Dictionary.com. Definition for "susceptible". Available via url < dictionary.reference.com/browse/susceptible>, printed on Jun. 5, 2012.*
Berwick and Vineis, "Markers of DNA repair and susceptibility to cancer in humans: an epidemiologic review," *J. of the National Cancer Institute*, 92 (11): 874-897, 2000.
Bonassi et al., "An increased micronucleus frequency in peripheral blood lymphocytes predicts the risk of cancer in humans," *Carcinogensis*, 28 (3): 625-631, 2007.
Bonassi et al., "Chromosomal aberrations and risk of cancer in humans: an epidemiologic perspective," *Cytogenet. Genome Res.*, 104 (1-4): 376-382, 2004.
Bonassi et al., "Human population studies with cytogenetic biomarkers: review of the literature and future prospectives," *Environ. Mol. Mutagen*, 45 (2-3): 258-270, 2005.
El-Zein et al., "Cytokinesis-blocked micronucleus cytome assay biomarkers identify lung cancer cases amongst smokers," *Cancer Epidemiol. Biomarkers Prev.*, 17 (5): 1111-1119, 2008.
El-Zein et al., "The cytokinesis-blocked micronucleus assay as a novel biomarker for lung cancer risk," *Cancer Res.*, 66 (12): 6449-6456, 2006.
Fenech et al., "HUMN project: detailed description of the scoring criteria for the cytokinesis-block micronucleus assay using isolated human lymphocyte cultures," *Mutation Research*, 534: 65-75, 2003.
Fenech, "A lifetime passion for micronucleus cytome-assay—reflections from down under," *Mutation Research*, 681: 111-117, 2009.
Fenech, "Biomarkers of genetic damage for cancer epidemiology," *Toxicology*, 181-182: 411-416, 2002.
Fenech, "Chromosomal biomarkers of genomic instability relevant to cancer," *Drug Discovery Today*, 7 (22): 1128-1137, 2002.
Fenech, "Cytokinesis-block micronucleus assay evolves into a 'cytome' assay of chromosomal instability, mitotic dysfunction and cell death," *Mutation Research*, 600: 58-66, 2006.
Fenech, "Cytokinesis-block micronucleus cytome assay," *Nature Protocols*, 2 (5): 1084-1104, 2007.
Fenech, "The cytokinesis-block micronucleus technique and its application to genotoxicity studies in human populations," *Environ. Health Prespect.*, 101(Sup. 3): 101-107, 1993.
Fenech, "The genome health clinic and genome health nutrigenomics concepts: diagnosis and nutritional treatment of genome and epigenome damage on an individual basis," *Mutagenesis*, 20 (4): 255-269, 2005.
Fenech, "The in vitro micronucleus technique," *Mutation Res.*, 455: 81-95, 2000.
Hill et al., "Gender differences in genetic damage induced by the tobacco-specific nitrosamine NNK and the influence on the Thr241Met polymorphism in the XRCC3 gene," *Environ. Mol. Mutagen*, 46 (1): 22-29, 2005.
Hirsch et al., "Future developments in the treatment of lung cancer," *Lung Cancer*, 38 (Sup. 3): S81-S85, 2002.
International Search Report and Written Opinion, issued in Int. App. No. PCT/US2007/70891, mail date Dec. 27, 2007.
Kimura et al., "Methylenetetrahydrofolate reductase C677T polymorphism, folic acid and riboflavin are important determinants of genome stability in cultured human lymphocytes," *J. Nutr.*, 134 (1): 48-56, 2004.
Lindberg et al., "Origin of nuclear buds and micronuclei in normal and folate-deprived human lymphocytes," *Mutation Research*, 617: 33-45, 2007.
Matthopoulos, "Dynamic analysis of DNA damage by flow cytometry and FISH," *The Scientific World Journal*, 15 (6): 563-570, 2006.
Offer et al., "A simple assay for frequency of chromosome breaks and loss (micronuclei) by flow cytometry of human reticulocytes," *The FASEB Journal*, 19: 485-487, 2005.
Rossignol et al., "Metabolism and DNA damage induced by 4-(methylnitrosamino)-1-(3-pyridyl)-1-butanone in fetal tissues of the syrian golden hamster," *Cancer Res.*, 49: 5671-5676, 1989.

(Continued)

*Primary Examiner* — Carla Myers
(74) *Attorney, Agent, or Firm* — Parker Highlander PLLC

(57) ABSTRACT

The present invention demonstrates the differential sensitivity of PBLs from lung cancer patients and healthy controls to NNK-induced genetic damage. The data provide convincing evidence that the preferred CBMN assay is a robust test for detection of this sensitivity and yields results that are a good predictor of, for example, lung cancer risk. The simplicity, rapidity, and sensitivity of the CBMN test make it a valuable tool for screening and, for example, prioritizing potential cases for early detection of the disease.

28 Claims, 3 Drawing Sheets

PUBLICATIONS

Shen et al., "Dietary folate intake and lung cancer risk in former smokers—a case-control study," *Cancer Epidemiol Biomarkers Prev.*, 12 (10): 980-986, 2003.

Shen et al., "Smoking, DNA repair and risk of non-small cell carcinoma of the lung," *Int. J. Cancer*, 107 (1): 84-88, 2003.

Smolewski et al., "Micronuclei Assay by laser scanning cytometry," *Cytometry*, 45 (1): 19-26, 2001.

Spitz et al., "Genetic susceptibility to lung cancer: the role of DNA damage and repair," *Cancer, Epidemiology, Biomarkers & Prevention*, 12: 689-698, 2003.

Stewenius et al., "Structural and numerical chromosomes changes in colon cancer develop through telomere-mediated anaphase bridges, not through mitotic multipolarity," *PNAS USA*, 102 (15): 5541-5546, 2005.

Thun et al., "Cigarette smoking and changes in the histopathology of lung cancer," *J. Natl. Cancer Inst.*, 89 (21): 1580-1586, 1997.

Tice et al., "Single cell gel/comet assay: guidelines for in vitro and in vivo genetic toxicology testing," *Environmental and Molecular Mutagensis*, 35 (3): 206-221, 2000.

Wei et al., "Reduced DNA repair capacity in lung cancer patients," *Cancer Res.*, 56: 4103-4107, 1996.

Wu et al., "Telomere dysfunction: a cancer predisposition factor?" *J. Natl. Cancer Inst.*, 95 (16): 1211-1218, 2003.

Wu et al., "XPA polymorphism associated with reduced lung cancer risk and a modulating effect on nucleotide excision repair capacity," *Carcinogenesis*, 24 (3): 505-509, 2003.

* cited by examiner

METHODS FOR ASSESSING CANCER SUSCEPTIBILITY TO CARCINOGENS IN TOBACCO PRODUCTS

The present application claims benefit of priority to U.S. Provisional Application Ser. No. 60/804,532 filed Jun. 12, 2006, the entire contents of which is hereby incorporated by reference.

The government owns rights in the present invention pursuant to National Cancer Institute grants CA55769, CA98549, CA70907, DMDD17-02-10707, FAMRI, and NIEHS ES07784.

BACKGROUND OF THE INVENTION

1. Field of the Invention

The present invention relates generally oncology and cancer susceptibility. More particularly, it concerns methods for assessing cancer susceptibility, particularly lung cancer susceptibility, to carcinogens in tobacco smoke and products.

2. Description of the Related Art

Lung cancer is the leading cause of cancer mortality in the United States, and there is an urgent need to improve outcome by identifying and validating markers to predict risk and allow early diagnosis (1). A crucial early event in carcinogenesis is the induction of the genomic instability phenotype, which enables an initiated cell to evolve into a cancer cell by achieving a greater proliferative capacity (2). It is well known that cancer results from an accumulation of multiple genetic changes that can be mediated through chromosomal changes and that have the potential to be cytogenetically detectable (3). It has been hypothesized that the level of genetic damage in peripheral blood lymphocytes reflects amount of damage in the precursor cells that lead to the carcinogenic process in target tissues (4). Evidence that cytogenetic biomarkers are positively correlated with cancer risk has been strongly validated in recent results from both cohort and nested case-control studies showing that chromosome aberrations are a marker of cancer risk (5-9) reflecting both the genotoxic effects of carcinogens and individual cancer susceptibility.

A number of epidemiologic studies employing a variety of measures of DNA repair capacity have been performed to compare cancer patients and healthy control subjects and thereby assess the role of repair capacity in cancer risk (19). Using a variety of in vitro assays, we have previously shown (41-45) that sensitivity to mutagens varies widely between subjects with and without cancer and that this variation translates into interindividual variability in susceptibility to in vitro carcinogenic challenge. The mutagen sensitivity assay measures indirectly an individual's DNA repair capacity from cellular damage remaining after an in vitro mutagenic exposure and subsequent recovery. This assay, developed by Hsu et al (46), reflects general and nonspecific impairment of the DNA repair machinery and host genomic stability.

More than 80% of lung cancers are attributed to tobacco exposure. However, since only a fraction of long-term smokers (~15%) will develop lung cancer in their lifetime (16), it is proposed that genetic factors play a role in individual susceptibility. An individual's DNA repair capacity may play a significant role in modifying risk for cancer. The tobacco-specific nitrosamine 4-(methylnitrosamino)-1-(3-pyridyl)-1-butanone (NNK) is a strong pulmonary carcinogen and is particularly important in the induction of adenocarcinoma, now the leading lung cancer subtype in the United States (17). Studies on the metabolism of NNK have shown that it induces cross-links in DNA; interacts with DNA, forming different types of adducts; and increases the frequency of chromosome aberrations (18, 19). Hecht (20) reported that DNA adducts derived from NNK are present at a higher level in lung tissues from lung cancer patients than controls, and metabolites of NNK are found in the urine of people who use tobacco products or are exposed to environmental tobacco smoke. The repair kinetics for NNK-induced genetic damage have not been clearly elucidated but may involve several DNA-repair pathways, including base excision and nucleotide excision repair pathways (21).

Tobacco smoke contains an array of potent carcinogens including polycyclic aromatic hydrocarbons, aromatic amines and N-nitrosamines. Among the polycyclic aromatic hydrocarbons, benzo [a] pyrene has been the most extensively studied, and our research to date has focused largely on this carcinogen. Benzo [a] pyrene is an effective pulmonary carcinogen, inducing predominantly squamous cell carcinoma upon intratracheal instillation into rats and hamsters. Tobacco-specific nitrosamines are found in high concentrations in mainstream smoke (28). The most potent carcinogenic member of this group, as shown in experimental animals, is NNK (29). NNK induces lung adenocarcinoma independent of route of administration and in both susceptible and resistant strains of mice (30). The estimated NNK dose of lifetime smokers (2 packs per day for 40 years) is 1.6 mg NNK per kilogram of body weight (31) close to the lowest dose shown to induce lung tumors in rats 1.8 mg (32). The total level of NNK in mainstream smoke is 3 to 15 times that of Benzo [a] pyrene (33). Gender differences and DNA repair allelic variants, have been reported to modulate the effect of NNK-induced genotoxic damage using the conventional chromosome aberration assay (24, 25) or fluorescence in situ hybridization assay using chromosome 1-specific probes in healthy smokers and nonsmoker controls (26). In addition, NNK was shown to be a potent mutagen using both the Ames Salmonella assay and the micronucleus test in Swiss mice (34).

The CBMN assay is a genotoxicity assay that provides simultaneous information on a variety of chromosomal damage endpoints that reflect chromosomal breakage, chromosome rearrangements, and gene amplification. In the current study, the frequencies of MN, NPBs, and NBUDs were significantly higher in the lung cancer patients than in controls. Cheng et al reported similar results after evaluating the MN frequency in 42 patients with lung cancer and 55 controls (35). The significantly higher spontaneous MN levels observed in the cases suggest a higher background level of genetic instability in the cancer patients. The effect of smoking on MN frequency in peripheral blood lymphocytes has not been consistent across studies, which generally have been small and not properly designed to detect the effect of smoking as the main outcome measure (36-38). However, a pooled re-analysis of 24 databases (5710 subjects, of which 1409 were current smokers) from the HUMN Project revealed that MN frequency was not influenced by the number of cigarettes smoked per day among subjects occupationally exposed to genotoxic agents, whereas a U-shaped curve was observed for nonexposed smokers, with a significant increase of MN frequency in individuals smoking 30 cigarettes or more per day (frequency ratio [FR]=1.59, 95% CI=1.35-1.88) (39).

This assay has been used to study susceptibility to other mutagenic agents. Scott et al (47) showed that individuals who developed breast cancer and their relatives were more sensitive than controls to the DNA-damaging effect of ionizing radiation, as demonstrated by MN frequency. This sensitivity was observed in 10 of 11 cases of BRACA1 mutation carriers and was indicative of a defect in double-strand break repair (48) thus suggesting that this assay is not only useful as a marker of DNA damage but also as a means of measuring the DNA repair phenotype. Umegaki and Fenech (11) recently validated the use of NPBs as a biomarker of DNA damage in a human B lymphoblastoid cell line (WIL2-NS). NPB frequency in binucleated cells increased up to 20 fold in the WIL2-NS cells relative to control cells in response to agents known to induce DNA strand breaks; the effects were found to be dose-dependant. Crott et al (49) recently reported that the frequency of NPBs and NBUDs correlated significantly and negatively with folic acid concentrations, suggesting that these chromosomal endpoints may be induced by folic acid deficiency. In addition, Kimura et al (50) showed a significant impact of methylene-tetrahydrofolate reductase (MTHFR) C677T polymorphism and folic acid concentration on MN, NPBs and NBUDS in human lymphocytes. Recently, scientists associated with the present inventors reported that polymorphisms in genes involved in folate metabolism were associated with lung cancer risk, an effect that may be modulated by dietary nutrient intake (51).

However, there is currently no known or reported method for actually predicting a subject's susceptibility to the development of smoking or tobacco-related cancers. There is no doubt that the development of such an assay would be of great medical importance, indeed, a medical breakthrough.

SUMMARY OF THE INVENTION

The present invention provides, for the first time, convenient, highly-predictive, and easy-to-perform methods for assessing cancer susceptibility of human subjects to carcinogens in tobacco smoke, particularly subjects that have not been diagnosed with such a cancer. In a preferred embodiment, in a general sense the method involves first obtaining a sample, wherein the sample includes nucleated cells (i.e., cells of a type having a nucleus) of the subject in question. The cell sample is then assayed to determine the frequency of chromosomal damage endpoints. From this assay, cancer susceptibility of the subject can then be assessed as a function of the amount of chromosomal damage endpoint frequency. It is contemplated that the present invention will have broad applicability to medical science in that it will permit, for example, the ability to identify those individuals that are particularly at-risk for tobacco smoke-related carcinogenesis, such as tobacco uses (e.g., cigarette, pipe or cigar smokers, or tobacco chewers or snuff users) so that such individuals can receive additional intensive follow up programs, such as smoking cessation therapy, close monitoring and screening programs (e.g., x-ray and CT-scanning). Thus, the invention will find particular applicability to screening of smokers or other at-risk individuals (e.g., those having a history of asbestos or radiation exposure, a family history of neoplasms, especially tobacco related neoplasms).

As noted, a particular advantage of the present invention is that it is generally applicable to the use of any nucleated cell type, i.e., any cell type having a nucleus and therefore forming chromosomal structures, in that a basis of the invention is testing for chromosomal damage in the subject being tested. Non-limiting examples of useful nucleated cell types include are reticulocytes, buccal cells, bladder wash cells, fibroblasts (skin, liver, etc.) or lymphocytes. However, due to ease and convenience of collecting, the most preferred cell types are lymphocytes, particularly peripheral blood lymphocytes, which are readily available from blood samples.

While the present invention is directed generally to susceptibility assessment of any cancer that is smoking related, it is believed to be particularly applicable to cancers such as lung cancer (adenocarcinoma is now the most prevalent lung cancer in the United States or squamous cell carcinoma), squamous cell carcinoma of the head and neck (SCCHN), bladder cancer, cancer of the throat and larynx, etc.

The inventors have discovered that the most convenient and useful, although not exclusive, method for determining the frequency of chromosomal damage endpoints is through the use of the well-known cytokinesis-block micronucleus assay (the "CBMN" assay) (reviewed in 27). This assay permits the quantification of chromosomal damage endpoints such as micronuclei ("MN"), nucleoplasmic bridges ("NPBs") and nuclear buds ("NBUDs"), typically determined as an average per selected number of cells examined. Moreover, although the manual CBMN assay is currently preferred, it has been successfully automated, for example, using laser flow cytometry (52, 53). While the CBMN assay is currently preferred, it is contemplated that virtually any assay capable of detecting and quantifying chromosomal damage endpoints, particularly those capable of detecting and quantifying MN, NPDs and/or NMUBs, can be employed. For example, assay techniques such as conventional screening for chromosome aberrations that can detect both structural and numerical aberrations (however this method requires highly trained personnel and is time consuming) alone and/or in combination with target-specific techniques such as FISH (which require very expensive probes and are not convenient for population screening) (54, 55). The so-called comet technique is another technique contemplated by the inventors (56), but, again, this is in no way intended to limit the invention.

An important discovery by the inventors is that the use of nucleated cells that have not been treated or challenged with tobacco smoke carcinogens such as nitrosamine 4-(methylnitrosamino)-1-(3-pyridyl)-1-butanone (NNK) will nonetheless give useful, predictive susceptibility results, particularly with respect to measuring chromosomal damage endpoints such as are further defined as spontaneous micronuclei (MN), nucleoplasmic bridges (NPDs) or nuclear buds (NBUDs). However, in preferred embodiments, the determination of chromosomal damage endpoints such as the foregoing will be carried out in nucleated cells that have been treated with tobacco smoke carcinogens such as nitrosamine 4-(methylnitrosamino)-1-(3-pyridyl)-1-butanone (NNK). Although the use of NNK is particularly preferred in the practice of the invention, it is contemplated that other tobacco carcinogens could be employed in the practice of the invention include virtually any known tobacco carcinogen such as benzo(a) pyrene and/or its metabolite BPDE.

In embodiments of the invention that involve scoring of MNs, NPDs, and/or NBUDs, it is typically preferred to score all three as this will generally give the most predictive result. However, this is not required as reasonably predictive results can be obtained by measuring only one of the three, or two of the three (such as NPBs/NBUDs, MNs/NPBs, MNs.NBUDs, NBUDs/NPBs). The latter approach may be preferred where, for example, an assay technique is employed that scores certain damage endpoints with a greater degree of accuracy or where multiple assay techniques are employed.

In a preferred practice of the assay of the invention, one will most typically score chromosome damage endpoints on a selected number of cells and the frequency of chromosomal damage endpoints thus determined or expressed as a per cell number average of the selected number of cells. The inventors typically prefer to perform the assay on at least about 1000 nucleated cells, but the invention does not exclude using smaller numbers, such as at least about 500, or even fewer. Of course, the determination of cell number will often never be exact and thus the foregoing numbers are expressed as averages and there will inherently be some variation in the number of cells scored.

Once the chromosome damage endpoints are quantified or averaged for cells of the particular subject, it is then preferred to compare the endpoint score realized for the test subject, whether the cells are carcinogen treated or not, against a control number, such as a control number that is representative of the population as a whole or selected subpopulations. Such may simply be a control number or a series of control numbers that is provided to the institution or entity that conducts the assays on members of the public often expressed with a standard variation or deviation, for population groups having varying degrees of cancer risk associated with that group.

One preferred means of generating such control numbers, as illustrated herein below, it to simply carry out the assay of the invention in population groups, such as representative population groups, preferably a group representative of the population as a whole (perhaps selected on the basis of age, gender, race, ethnicity country of residence, food preferences, etc.), and averaging the endpoint score across the selected population again preferably expressed along with variation or deviation. Thus, results obtained for the subject can then be compared to the control listings and in this manner, the subject can be quickly informed of his or her risk category, not unlike what is commonly done today in the case of cholesterol measurement and management. Thus, in a general sense, a higher number of chromosomal damage endpoints as compared to a control number will be indicative of a higher cancer risk, and the higher the number over the control, the higher the cancer risk.

Indeed, provided herein below is a summary chart that provides convenient risk assessment damage endpoints versus control population means and median for each of the three preferred chromosome damage endpoints, MN, NPBs and NBUDs. Here, for example, an about 2 fold increase or more in risk is assigned for every unit increase in baseline or NNK-induced MN versus the control. Further, in the case of NPBs, an approximately 29 or greater fold increase in risk is assigned for every unit increase in baseline or NNK-induced NPBs versus the control, in particular, about a 45 fold or greater increase in risk is assigned for every unit increase in NNK-induced versus the control. Likewise, with respect to NBUDs, approximately about a 6 fold increase or greater in risk is assigned for every unit increase baseline or NNK-induced NBUDs versus the control, and in particular, about a 10 fold increase in risk is assigned for every unit increase in NNK-induced NBUDs versus the control.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE PREFERRED EMBODIMENTS

A. Introduction

Figure 1A:
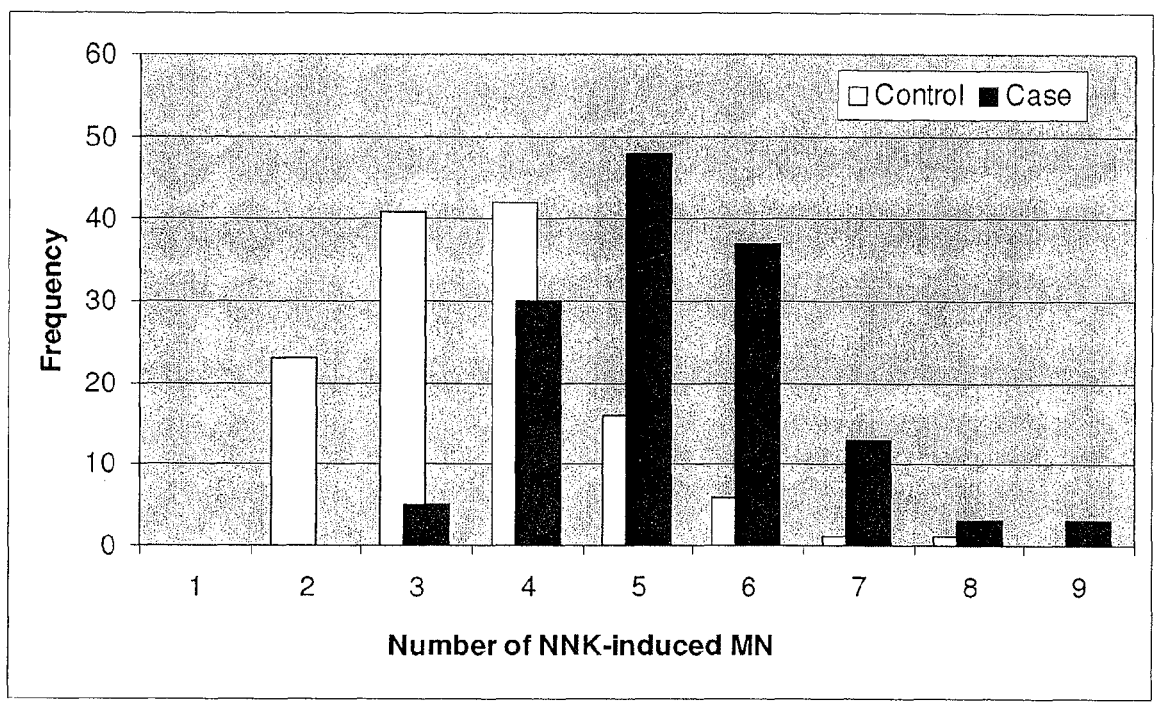
FIG. 1A-C: A. Frequency of NNK-induced micronuclei (MN) by cases-controls status. Forty percent of the cases had >5 MN, versus 6% of the controls. B. Frequency of NNK-induced nucleoplasmic bridges (NPBs) by cases-controls status. Eighty nine percent of the cases had >6 NPBs, versus 0% of the controls. C. Frequency of NNK-induced nuclear buds (NBUDs) by cases-controls status. Twenty-three percent of the cases had >2 bud, versus 2% controls.

There are a variety of biomarkers evaluating susceptibility to the carcinogenic effects of benzo [a] pyrene; however, to the inventors knowledge no assays specifically evaluate susceptibility to the nicotine-derived nitrosamine 4-(methylnitrosamino)-1-(3-pyridyl)-1-butanone (NNK), a potent inducer of lung adenocarcinoma. In the present invention, developed out of a case-control study, the inventors exemplified the invention through the use of a modification of the cytokinesis-block micronucleus (CBMN) assay, an established biomarker for DNA damage and genomic instability, to evaluate susceptibility to NNK by measuring the frequency of NNK-induced chromosomal damage endpoints (micronuclei [MN]; nucleoplasmic bridges [NPBs] and nuclear buds [NBUDs]) per 1000 binucleated peripheral blood lymphocytes.

In this study, described in more detail hereinbelow, levels of both spontaneous and NNK-induced chromosomal damage were found to be significantly higher in lymphocytes from 139 lung cancer patients than those from 130 matched controls. Forty-seven percent of the cases (compared with 12% of the controls) had ≧4 spontaneous MN, 66% of the cases (and no controls) had ≧4 spontaneous NPBs, and 25% of cases (versus 5% of controls) had >1 spontaneous NBUDs (P<0.001). Similarly, 40% of the cases (versus 6% of the controls) had ≧5 NNK-induced MN, 89% of the cases (and no controls) had ≧6 induced NPBs, and 23% of the cases (versus 2% of the controls had >2 induced NBUDs (P<0.001). When analyzed on a continuous scale, spontaneous MN, NPBs and NBUDs were associated with 2-, 29-, and 6-fold increases in risk for cancer respectively. Similarly, NNK-induced risks were 2.3-, 45.5-, and 10-fold.

The inventors further evaluated the use of results from the CBMN assay to predict cancer risk based on the numbers of MN, NPBs, and NBUDs defined by percentile cut-points in control data. The probabilities of being a cancer patient were 96%, 98% and 100% when using the 95th percentiles of spontaneous and NNK-induced MN, NPBs and NBUDs, respectively, in combination. This study, quits surprisingly, indicates that the CBMN assay is extremely sensitive to NNK-induced genetic damage and that the assay results serve as a strong predictor of lung cancer risk.

B. The CBMN Assay

The cytokinesis-block micronucleus (CBMN) assay, typically employed in human lymphocytes, is one of the most commonly used methods for measuring DNA damage because it is relatively easier to score micronuclei (MN) than chromosome aberrations (2). MN originate from chromosome fragments or whole chromosomes that fail to engage with the mitotic spindle and therefore lag behind when the cell divides. Compared to other cytogenetic assays, quantification of MN confers several advantages, including speed and ease of analysis, no requirement for metaphase cells and reliable identification of cells that have completed only one nuclear division. This prevents confounding effects caused by differences in cell division kinetics because expression of MN, NPBs or NBUDs is dependent on completion of nuclear division (10). Because cells are blocked in the binucleated stage, it is also possible to measure nucleoplasmic bridges (NPBs) originating from asymmetrical chromosome rearrangements and/or telomere end fusions (11, 12). NPBs occur when the centromeres of dicentric chromosomes or chromatids are pulled to the opposite poles of the cell at anaphase. In the CBMN assay, binucleated cells with NPBs are easily observed because cytokinesis is inhibited, preventing breakage of the anaphase bridges from which NPBs are derived, and thus the nuclear membrane forms around the NPB. Both MN and NPBs occur in cells exposed to DNA-breaking agents (13, 14). In addition to MN and NPBs, the CBMN assay allows for the detection of nuclear buds (NBUDs), which represent a mechanism by which cells remove amplified DNA and are therefore considered a marker of possible gene amplification (reviewed by Fenech (14). The CBMN test is gradually replacing the analysis of chromosome aberrations in lymphocytes because MN, NPBs and NBUDs are easy to recognize and score and the results can be obtained in a shorter time (15). Furthermore, it should be noted that the CBMN assay has been automated with some degree of success (52, 53), including the use of laser scanning cytometry or laser flow cytometry, and future improvements are expected.

C. Other Assays for Chromosomal Damage Endpoints

As noted, there are other techniques that could be employed to assess and quantify chromosomal damage endpoints. One such technique is to simply employ conventional chromosome analysis directly or in combination with the well-known FISH technique (54, 55) which employs fluorescent chromosomal probes and automated scanning capability. Additionally, other assays such as the comet assay, also called the single cell gel electrophoresis assay (SCGE assay) could be employed (56). The comet assay is a sensitive and rapid method for detecting DNA single- and double-strand breaks and DRC in individual cells. The use of this assay has increased in the past few years, especially in genotoxicity testing and biomonitoring. This assay is simpler, less expensive and more objective than the mutagen sensitivity assay. The assay only requires a small number of cells that are suspended in a thin agarose gel on a microscope slide, then lysed, electrophoresed, and stained with a fluorescent DNA binding dye. The electric current pulls the charged DNA from the nucleus, leading to preferential migration of negatively charged, relaxed and broken DNA fragments. Fluorescence imaging of these nuclei reveals cells with damaged DNA migrating toward the anode, forming an appearance analogous to a 'comet' with a bright head and a tail. The comet assay uses image analysis that allows for reduced observer bias, and permits densitometric as well as geometric measurements. The present inventors and others have demonstrated that the comet assay can be used to measure DNA damage or repair as a cancer susceptibility marker.

D. Clinical Study

1. Study Population

Cases and controls for the analysis that forms the basis of this invention were accrued from an ongoing molecular epidemiologic study on susceptibility markers for lung cancer. Cases (n=139) were consecutive patients with newly diagnosed, previously untreated, histologically confirmed lung cancer patients. All cases were recruited from The University of Texas M. D. Anderson Cancer Center, with no age, gender, ethnicity, tumor histology, or disease stage restrictions. Healthy controls (n=130) were recruited from the Kelsey-Seybold Clinics, Houston's largest private multispecialty physician group. Controls were matched to the cases on age (±5 years), gender, ethnicity, and smoking status (current and former). Data related to the subjects' medical history, family history of cancer, smoking habits, and occupational history were obtained through an interviewer-administered risk-factor questionnaire and by review of an institutional electronic patient history database. After giving informed consent, all study participants donated a 10 mL blood sample, which was drawn into coded heparinized tubes.

2. PBL Cultures for CBMN Test

The CBMN test was performed using the cytochalasin B technique described by Fenech and Morley (22) and following recommendations from The International Collaborative Project on Micronucleus Frequency in Human Populations (HUMN Project) to measure MN, NPBs and NBUDs in untreated cells and NNK-treated cells (27). Duplicate lymphocyte cultures were prepared for each study subject. Each culture contained $2.0 \times 10^6$ cells in 5 mL RPMI 1640 medium supplemented with 100 U/mL penicillin, 100 µg/mL streptomycin, 10% fetal bovine serum, and 2 mM L-glutamine (Gibco-Invitrogen, Carlsbad, Calif.) and 1% phytohemagglutinin (Remel, Lenexa, Kans.). For the cultures treated with NNK, 24 hours after initiation, the PBLs were centrifuged and the supernatant growth medium was removed and reserved. The PBLs were resuspended in 5 mL of serum-free RPMI 1640 medium supplemented with 0.24 mM NNK (a dose previously used by us and others (23-26) (CAS No. 64091-91-4, National Cancer Institute, Midwest Carcinogen Repository, Kansas City, Mo.; purity>98%) and incubated at 37° C. in the presence of 5% $CO_2$ for 2 hours.

Next, the PBLs were washed twice with serum-free RPMI 1640, transferred to clean tubes and re-incubated for 48 hours in the reserved supernatant. At 44 hours after initiation, cells were blocked in cytokinesis by adding cytochalasin B (Sigma, St. Louis, Mo.; final concentration 4 g/mL). Similarly, cultures for the determination of spontaneous damage (untreated cells) were handled in the same manner, with the exception of treatment with NNK. The total incubation time for all cultures was 72 hours. After incubation, the cells were fixed in 3:1 methanol:glacial acetic acid, dropped onto clean microscopic slides, air-dried and stained with Giemsa stain. For each sample, 1000 binucleated cells were scored blindly using a Nikon E-400 light optical microscope following the scoring criteria outlined by HUMN Project (2,22,27); the numbers of MN, NPBs, and NBUDs per 1000 binucleated cells were recorded. For quality control, 20% of the slides were randomly selected and blindly rescored and the results compared with the original scoring.

3. Statistical Analysis

All analyses were performed using the Intercooled Stata 8.0 statistical software package (Stata Corp., College Station, Tex.). Pearson's $\chi^2$ test was used to test for differences between the cases and controls in terms of gender, alcohol consumption, and family history of cancer. Student's t test was used to test differences in mean age and average number of cigarettes smoked per day. The inventors used the nonparametric Wilcoxon rank-sum test (continuous) and the Pearson's $\chi^2$ test (categorical) to compare the distribution of spontaneous and NNK-induced MN, NPBs and NBUDs between the cases and controls. Dot charts were also constructed using S-Plus (v. 6.2, Insightful Corp., 2003) to compare the distribution of spontaneous and NNK-induced MN, NPBs, and NBUDs between the cases and controls. Odds ratios (ORs) and 95% confidence intervals (CIs) were calculated to provide an estimate of the risk of lung cancer associated with the number of spontaneous and NNK-treated MN, NPBs, and NBUDs per 1000 cells. Unconditional multivariable logistic regression analysis was used to control for confounding by age, gender, alcohol consumption, smoking status, and years smoked.

4. Demographics and the Study Population

The demographic characteristics of the 139 cases and 130 controls are summarized in Table 1. Cases and the controls did not differ significantly in terms of gender. However, on average, the cases were 2.5 years younger (mean age±SE=58.4±0.41) than the controls (mean age±standard error [SE]=60.9±0.32) (P<0.001). Twenty-four percent of the patients self-reported a family history of cancer in first-degree relatives, compared with 22% of the controls (P=0.780). Cases had on average smoked cigarettes for 42.1 years, compared with 37.7 years for controls (P<0.001), but both groups smoked about the same number of cigarettes per day (mean number of cigarettes per day±SE for cases=30.2±1.38 and for controls=29.2±1.21; P=0.651).

TABLE 1

Distribution of selected host characteristics by case-control status*

| Variable | Case patients (n = 139) | Control subjects (n = 130) | P value[†] |
|---|---|---|---|
| Age, mean (standard error), years | 58.4 (0.41) | 60.9 (0.32) | <.001 |
| Gender, no. (%) | | | |
| Men | 97 (69.8) | 93 (71.5) | |
| Women | 42 (30.2) | 37 (28.5) | .752 |
| Family history of cancer, no. (%) | | | |
| No | 106 (76.3) | 101 (77.7) | |
| Yes | 33 (23.7) | 29 (22.3) | .780 |
| History of alcohol use, no. (%)[1] | | | |
| Yes | 91 (65.5) | 65 (50.0) | |
| No | 47 (33.8) | 59 (45.4) | .003 |
| Cigarette smoking, mean (standard error) | | | |
| No. years smoked[2] | 42.1 (0.50) | 37.7 (0.84) | <.001 |
| No. cigarettes smoked per day[3] | 30.0 (1.38) | 29.2 (1.21) | .651 |

*All study subjects are self-reported Caucasians and current smokers
[†]P values were derived from the $\chi^2$ test for categorical variables and Student's t test for continuous variables. All P values are two-sided
[1]Data were missing for 1 case and 6 controls
[2]Data were missing for 1 case
[3]Data were missing for 6 cases and 2 controls

5. Frequencies of Cytogenetic Endpoints by Case-Control Status

Overall, the lung cancer cases exhibited significantly higher values of all cytogenetic endpoints than the controls (Table 2). The P values for all Wilcoxon rank-sum tests were <0.001.

TABLE 2

Overall Spontaneous and NNK-induced frequencies of MN, NPBs, and NBUDs per 1000 binucleated cells by age, gender, and years smoked in lung cancer cases and controls

| | | Case Mean ± SE | Median | Control Mean ± SE | Median |
|---|---|---|---|---|---|
| | | SPONTANEOUS | | | |
| Overall | MN | 3.41 ± 0.13 | 3.0 | 1.98 ± 0.12 | 2.0 |
| | NPBs | 4.14 ± 0.10 | 4.0 | 0.57 ± 0.07 | 0.0 |
| | NBUDs | 0.28 ± 0.04 | 0.0 | 0.05 ± 0.02 | 0.0 |
| Males | MN | 3.47 ± 0.17 | 3.0 | 1.95 ± 0.13 | 2.0 |
| | NPBs | 4.13 ± 0.12 | 4.0 | 0.57 ± 0.08 | 0.0 |
| | NBUDs | 0.29 ± 0.05 | 0.0 | 0.06 ± 0.03 | 0.0 |
| Females | MN | 3.26 ± 0.25 | 3.0 | 2.05 ± 0.18 | 2.0 |
| | NPBs | 4.17 ± 0.16 | 4.5 | 0.57 ± 0.13 | 0.0 |
| | NBUDs | 0.26 ± 0.07 | 0.0 | 0.0 ± 0.0 | 0.0 |
| Age ≦ 62 | MN | 3.44 ± 0.15 | 3.0 | 1.97 ± 0.14 | 2.0 |
| | NPBs | 4.02 ± 0.12 | 4.0 | 0.55 ± 0.09 | 0.0 |
| | NBUDs | 0.25 ± 0.04 | 0.0 | 0.05 ± 0.02 | 0.0 |
| Age > 62 | MN | 3.34 ± 0.27 | 3.0 | 1.98 ± 0.18 | 2.0 |
| | NPBs | 4.44 ± 0.16 | 5.0 | 0.60 ± 0.11 | 0.0 |
| | NBUDs | 0.39 ± 0.10 | 0.0 | 0.05 ± 0.03 | 0.0 |
| YEARS SMOKED ≦ 32 | MN | 3.50 ± 0.42 | 3.5 | 1.88 ± 0.21 | 2.0 |
| | NPBs | 3.50 ± 0.38 | 3.0 | 0.42 ± 0.12 | 0.0 |
| | NBUDs | 0.13 ± 0.13 | 0.0 | 0.0 ± 0.0 | 0.0 |
| Years smoked > 32 | MN | 3.43 ± 0.14 | 3.0 | 2.00 ± 0.13 | 2.0 |
| | NPBs | 4.13 ± 0.10 | 4.0 | 0.61 ± 0.09 | 0.0 |
| | NBUDS | 0.29 ± 0.04 | 0.0 | 0.06 ± 0.03 | 0.0 |
| History of Alcohol Use Yes | MN | 3.47 ± 0.16 | 3.00 | 2.00 ± 0.15 | 2.00 |
| | NPBs | 4.19 ± 0.13 | 4.00 | 0.58 ± 0.11 | 0.00 |
| | NBUDs | 0.29 ± 0.05 | 0.00 | 0.07 ± 0.03 | 0.00 |
| History of Alcohol Use No | MN | 3.32 ± 0.23 | 3.00 | 1.88 ± 0.16 | 2.00 |
| | NPBs | 4.02 ± 0.16 | 4.00 | 0.55 ± 0.10 | 0.00 |
| | NBUDs | 0.27 ± 0.07 | 0.00 | 0.03 ± 0.02 | 0.00 |
| | | NNK-INDUCED | | | |
| Overall | MN | 4.32 ± 0.10 | 4.0 | 2.62 ± 0.10 | 3.0 |
| | NPBs | 8.12 ± 0.19 | 8.0 | 2.38 ± 0.09 | 2.0 |
| | NBUDs | 1.07 ± 0.09 | 1.0 | 0.12 ± 0.03 | 0.0 |
| Males | MN | 4.37 ± 0.13 | 4.0 | 2.63 ± 0.11 | 3.0 |
| | NPBs | 8.07 ± 0.23 | 8.0 | 2.27 ± 0.10 | 2.0 |
| | NBUDs | 1.07 ± 0.11 | 1.0 | 0.12 ± 0.03 | 0.0 |
| Females | MN | 4.19 ± 0.17 | 4.0 | 2.51 ± 0.23 | 2.0 |
| | NPBs | 8.24 ± 0.32 | 8.0 | 2.68 ± 0.19 | 2.0 |
| | NBUDs | 1.07 ± 0.12 | 1.0 | 0.11 ± 0.05 | 1.0 |
| Age ≦ 62 | MN | 4.22 ± 0.11 | 4.0 | 2.58 ± 0.14 | 2.0 |
| | NPBs | 8.11 ± 0.23 | 8.0 | 2.41 ± 0.11 | 2.0 |
| | NBUDs | 1.12 ± 0.11 | 1.0 | 0.13 ± 0.04 | 0.0 |
| Age > 62 | MN | 4.54 ± 0.22 | 4.0 | 2.75 ± 0.15 | 3.0 |
| | NPBs | 8.15 ± 0.33 | 8.0 | 2.35 ± 0.14 | 2.0 |
| | NBUDs | 0.90 ± 0.17 | 1.0 | 0.10 ± 0.05 | 0.0 |
| YEARS SMOKED ≦ 32 | MN | 3.63 ± 0.32 | 4.0 | 2.33 ± 1.02 | 2.0 |
| | NPBs | 9.25 ± 0.96 | 8.3 | 2.36 ± 0.19 | 2.0 |
| | NBUDs | 1.13 ± 0.44 | 1.0 | 0.06 ± 0.04 | 0.0 |
| Years smoked > 32 | MN | 4.33 ± 0.10 | 4.0 | 2.69 ± 0.12 | 3.0 |
| | NPBs | 8.07 ± 0.19 | 8.0 | 2.39 ± 0.09 | 2.0 |
| | NBUDS | 1.08 ± 0.01 | 1.0 | 0.13 ± 0.04 | 0.0 |
| History of Alcohol Use Yes | MN | 4.37 ± 0.14 | 4.00 | 2.61 ± 0.15 | 2.00 |
| | NPBs | 8.14 ± 0.24 | 8.00 | 2.32 ± 0.12 | 2.00 |
| | NBUDs | 1.04 ± 0.11 | 1.00 | 0.11 ± 0.04 | 0.00 |
| History of Alcohol Use No | MN | 4.26 ± 0.14 | 4.00 | 2.54 ± 0.15 | 3.00 |
| | NPBs | 8.04 ± 0.32 | 8.00 | 2.40 ± 0.13 | 2.00 |
| | NBUDs | 1.09 ± 0.18 | 1.00 | 0.14 ± 0.04 | 0.00 |

6. Frequencies of Spontaneous Cytogenetic Endpoints

Data on spontaneous MN, NPB, and NBUD frequencies by age, gender, and years of smoking are summarized in Table 2. Table 3 shows that approximately 47% of the cases had ≧4 MN/1000 binucleated cells, compared with 12% of control subjects, and that 40% of the control subjects had 0 or 1 MN, compared with only 9% of the cases (P<0.001). The mean number of spontaneous MN was significantly higher in the cases (mean+SE=3.41±0.13) than in the control subjects (mean+SE=1.98±0.12) (P<0.001). Similarly, about 66% of the cases had ≧4 NPBs, compared with none of the control subjects, while 86% of the controls had 0 or 1 NPB, compared with none of the cases (P<0.001). Furthermore, the number of spontaneous NPBs was significantly higher in the cases (mean+SE=4.14±0.10) than in the controls (mean+SE=0.57±0.07) (P<0.001).

With regard to frequency of NBUDs distribution, approximately 95% of the controls exhibited no spontaneous buds, compared with 73% of cases. Only 5% of the controls had 1 spontaneous bud, compared with one-quarter of the cases (P<0.001). Overall, the average number of spontaneous buds was significantly higher in the cases than in the controls (mean+SE=0.28±0.04 and 0.05±0.02 respectively) (P<0.001). No substantial differences were detected when the frequencies of MN, NPBs and NBUDs were stratified by gender, age, family history of cancer, number of years smoked, number of cigarettes per day, tumor histology, or disease stage. When the spontaneous MN data were analyzed as a continuous variable, using multivariate logistic regression, there was a 2.06-fold increase in lung cancer risk (95% CI=1.60 to 2.65) for each one-unit increase in MN frequency. Similarly, when spontaneous NPBs were analyzed as a continuous variable, there was a 29.05-fold increase in lung cancer risk (95% CI=7.48 to 112.80) for each one-unit increase in NPBs. For the NBUDs, there was a 6.5-fold increase in lung cancer risk (95% CI=2.37 to 18.01) for each one-unit increase in spontaneous bud frequency (Table 3).

TABLE 3

Distributions and risk estimates of lung cancer for spontaneous and NNK-induced MN, NPBs and NBUDs

| Variable | Case Patients, No. (%) | Control Subjects, No. (%) | OR (95% CI)* or P value[†] |
|---|---|---|---|
| MN | | | |
| Pearson's $\chi^2$ test | | | |
| Spontaneous | | | |
| 0 or 1 | 13 (9.4) | 52 (40.0) | |
| 2 or 3 | 61 (43.9) | 63 (48.5) | |
| ≧4 | 65 (46.8) | 15 (11.5) | P < .001 |
| NNK-induced | | | |
| 1 or 2 | 5 (3.6) | 64 (49.2) | |
| 3 or 4 | 78 (56.1) | 58 (44.6) | |
| ≧5 | 56 (40.3) | 8 (6.2) | P < .001 |
| Multivariate Logistic Regression analysis | | | |
| Spontaneous | 139 | 130 | OR = 2.06 (1.60-2.65) |
| NNK-induced | 139 | 130 | OR = 2.32 (2.32-4.80) |
| NPBs | | | |
| Pearson's $\chi^2$ test | | | |
| Spontaneous | | | |
| 0 or 1 | 0 (0.0) | 112 (86.2) | |
| 2 or 3 | 48 (34.5) | 18 (13.9) | |
| ≧4 | 91 (65.5) | 0 (0.0) | P < .001 |
| NNK-induced | | | |
| 0 or 2 | 0 (0.0) | 84 (64.6) | |
| 3 or 5 | 15 (10.8) | 46 (35.4) | |
| ≧6 | 124 (89.2) | 0 (0.0) | P < .001 |
| Multivariate Logistic Regression analysis | | | |
| Spontaneous | 139 | 130 | OR = 29.05 (7.48-112.80) |
| NNK-induced | 139 | 130 | OR = 45.52 (4.48-422.17) |
| NBUDs | | | |
| Pearson's $\chi^2$ test | | | |
| Spontaneous | | | |
| 0 | 102 (73.4) | 122 (95.3) | |
| 1 | 35 (25.2) | 6 (4.7) | |
| 2 | 2 (1.4) | 0 (0.0) | P < .001 |
| NNK-induced | | | |
| 0 | 48 (34.5) | 113 (86.9) | |
| 1 | 59 (42.5) | 15 (11.5) | |
| ≧2 | 32 (23.0) | 2 (1.5) | P < .001 |
| Multivariate Logistic Regression analysis | | | |
| Spontaneous | 139 | 130 | OR = 6.53 (2.37-18.01) |
| NNK-induced | 139 | 130 | OR = 10.10 (4.67-21.87) |

*Adjusted by age, gender, history of alcohol use, number of years smoked, and number of cigarettes smoked per day.
[†]P values are derived from the Pearson's $\chi^2$ test and are two-sided.

7. Frequencies of NNK-Induced Cytogenetic Endpoints

Figure 1B:
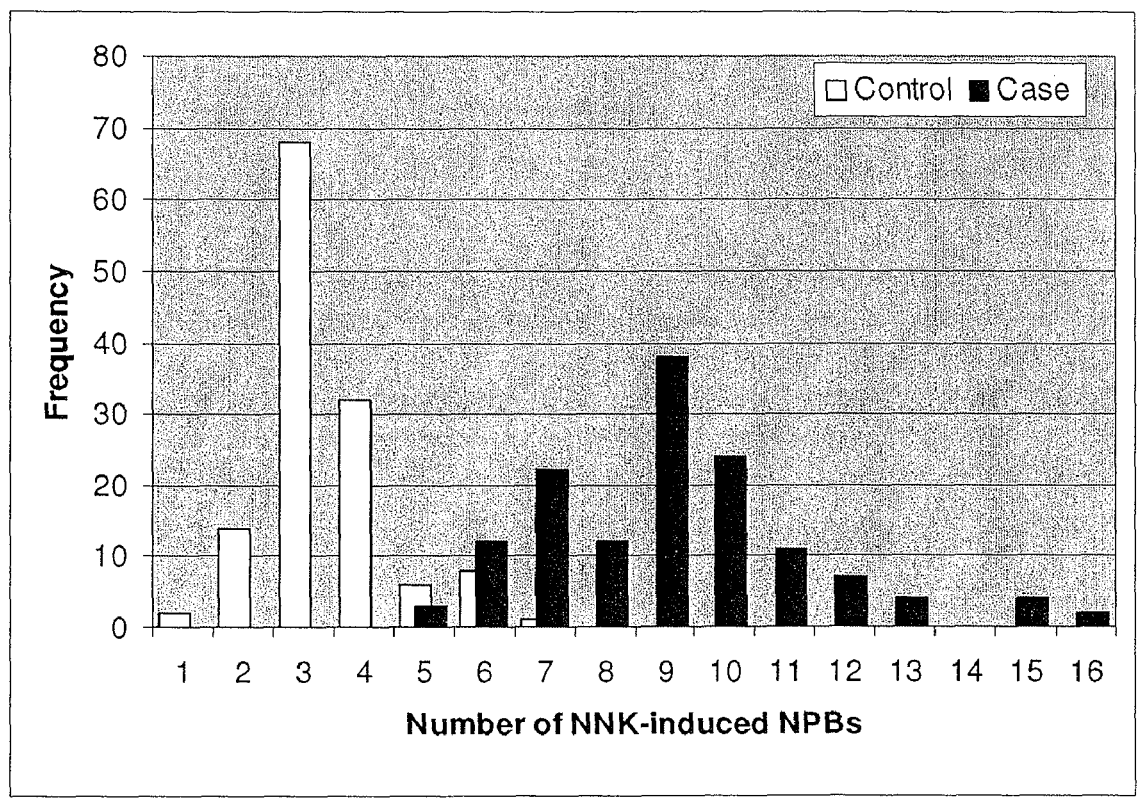

Data on NNK-induced MN, NPB, and NBUDs frequencies by age, gender, and smoking status are also summarized in Table 2. Table 3 shows that substantially more cases had ≧5 NNK-induced MN/1000 binucleated cells than controls (40% versus 6%); conversely far fewer cases than controls had only 1 or 2 NNK-induced MN (4% versus 49%; P<0.001) (FIG. 1A). The differences were even more pronounced for spontaneous and NNK-induced NPBs. The mean number of NNK-induced MN was significantly higher in cases (mean+SE=4.32±0.10) than in controls (mean+SE=2.62±0.10) (P<0.001). As reported in Table 3, approximately 89% of the case patients had ≧6 NNK-induced NPBs, compared with none of the control subjects. Conversely, 65% of the control subjects had 0 to 2 NNK-induced NPBs, compared with none of the case patients (P<0.001) (FIG. 1B). The number of NNK-induced NPBs was also significantly higher in cases (mean+SE=8.12±0.19) than in controls (mean+SE=2.38±0.09) (P<0.001).

There were no substantial differences when the frequencies of NNK-induced MN and NPBs were stratified by gender, age, family history of cancer, number of years smoked, number of cigarettes per day, tumor histology, or disease stage. When the NNK-induced MN data were analyzed as a continuous variable, there was a 2.32-fold increase in lung cancer risk (95% CI=2.32 to 4.80) for each one-unit increase in NNK-induced MN. Similarly, NNK-induced NPBs showed a 45.52-fold increase in lung cancer risk (95% CI=4.48 to 422.17) for each one-unit increase in frequency.

Figure 1C:
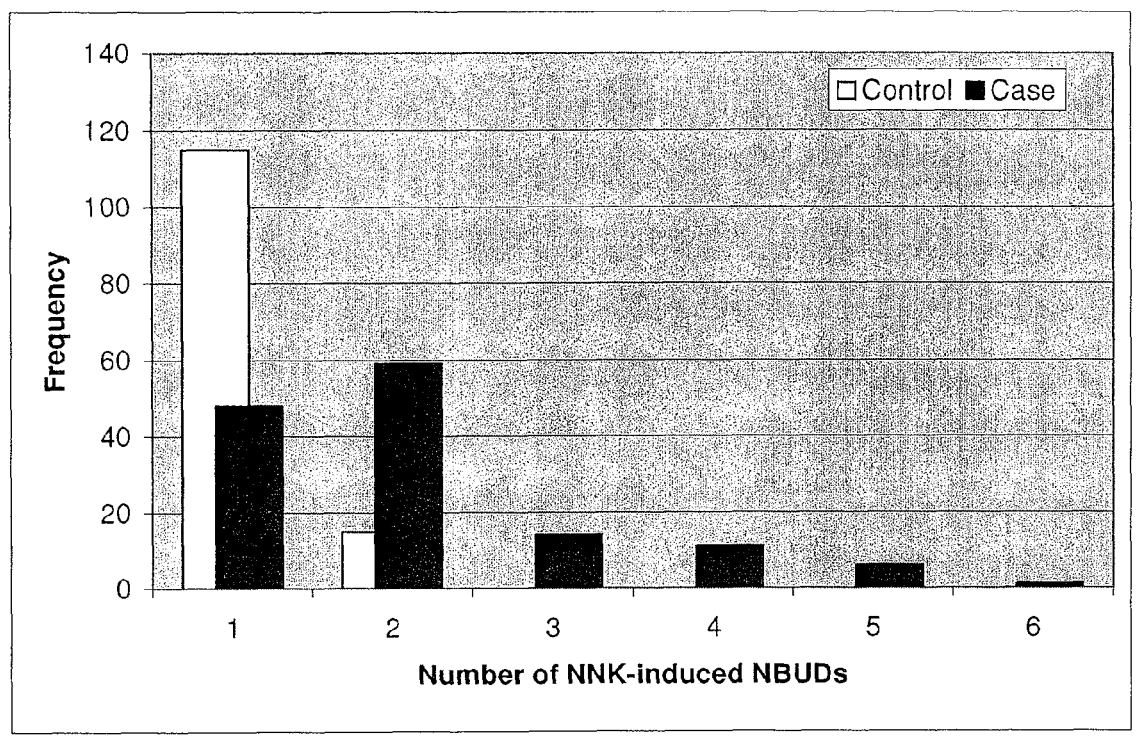

With regard to bud distribution, 23% of the cases had ≧2 NNK-induced buds compared with approximately 2% of controls; 87% of the controls had no NNK-induced buds, compared with 35% of the case patients (P<0.001) (FIG. 1C). The number of NNK-induced buds was significantly higher in cases than in controls (mean+SE=1.07±0.09 and 0.12±0.03 respectively) (P<0.001). When the NBUDs frequency was analyzed as a continuous variable, there was a 10.1-fold increase in lung cancer risk (95% CI=4.67 to 21.87) for each one-unit increase in NNK-induced buds. Similar patterns of difference between the cases and controls were observed for MN, NPBs and NBUDs within subgroups of subjects stratified by gender, age, family history of cancer, number of years smoked, number of cigarettes per day, tumor histology and disease stage (Table 3).

To ensure quality control, 20% of the slides were randomly selected for blind rescoring. Agreement between the original data and rescored data was measured using the Cohen's kappa statistical test. A statistically significant value of P<0.001 was obtained for both spontaneous and NNK-induced parameters, indicating that the agreement between the original and rescore data was not attributable to random chance.

8. CBMN Assay Results as a Predictor of Case-Control Status

Using the 75 percentile of the controls as a cut-off, the sensitivity of the CMBN assay was 96.4%, 100% and 100% for the MN, NPBs and the NBUDs respectively. The specificity of the assay was 93.0%, 100% and 100% for the MN, NPBs and the NBUDs respectively. The probabilities that a study subject was a case based on various cutpoints for the numbers of MN, NPBs, and NBUDs were calculated (Table 4). The numbers of MN, NPBs, and NBUDs were defined by percentile cutpoints in the control data. The probability of being a case increased as the percentile cutpoints increased for high numbers of MN, NPBs, or NBUDs. The numbers of spontaneous and NNK-induced MN showed no difference in terms of predictive capacity at the $90^{th}$ percentile. The numbers of spontaneous and NNK-induced NPBs showed a slight difference in terms of predictive capacity at the $90^{th}$ percentile, with the number of induced NPBs having a better predictive capacity than that of spontaneous NPBs. The number of NNK-induced NBUDs showed the highest predictive capacity of the three endpoints at and above the $85^{th}$ percentile. On combining all three endpoints and by using the 75 percentile of the controls as a cut-off, the CBMN assay sensitivity for detecting NNK-induced damage was 96.4%, with 80.8% specificity and 84.3% positive predictive value.

TABLE 4

Probability of being a case based on various percentile cutpoints for the numbers of MN, NPBs, and NBUDs in the controls

| Percentile of Controls | Spontaneous | | | NNK-induced | | | NNK-induced | | |
|---|---|---|---|---|---|---|---|---|---|
| — | MN | NPBs | NBUDS | MN | NPBs | NBUDS | MN | NPBs | NBUDS |
| 75 | 70.1 | 72.8 | 86.0 | 67.0 | 75.1 | 85.8 | 85.6 | 84.3 | 82.4 |
| 80 | 70.1 | 72.8 | 86.0 | 67.0 | 75.1 | 85.8 | 85.6 | 84.3 | 82.4 |
| 85 | 70.1 | 72.8 | 86.0 | 81.3 | 75.1 | 100.0 | 85.6 | 89.7 | 100.0 |
| 90 | 81.3 | 88.5 | 86.0 | 81.3 | 90.8 | 100.0 | 95.6 | 96.3 | 100.0 |
| 95 | 81.3 | 88.5 | 86.0 | 87.5 | 94.4 | 100.0 | 95.6 | 98.2 | 100.0 |

E. Discussion

In the foregoing study used to develop and exemplify the invention, the inventors tested the sensitivity of the study subjects' lymphocytes to the tobacco specific nitrosamine NNK, since it represents an important class of carcinogens known to be associated with the development of lung cancer, particularly adenocarcinoma, which is now the leading lung cancer histologic subtype in the United States, having surpassed squamous cell carcinoma (17). The results demonstrate that cases and controls had differential sensitivity to the genotoxic effects of NNK. The lymphocytes from patients with lung cancer were significantly more sensitive to NNK, with 1.6-, 3.4-, and 8.9-fold increases in MN, NPB, and NBUD frequencies, respectively, over controls. The results of this analysis also show that NNK-induced cytogenetic damage (expressed in teems of MN, NPB and NBUD frequencies) appears to be a highly sensitive predictor of lung cancer status.

The results showed no significant association between MN frequency and age, gender, or smoking status, which is in agreement with the results reported by Cheng et al (35). The current study is, to the inventors' knowledge, the first to report a significantly higher frequency of spontaneous NPBs and NBUDs in a lung cancer case-control study, thus supporting the hypothesis of breakage-fusion-bridge (BFB) cycle mechanism of hypermutation during carcinogenesis (reviewed in 2, 13). Gisselsson et al (40) reported that abnormal nuclear morphology (associated with NPBs, MN, NBUDs) is indicative of significant genomic instability within cells and is a common feature of a wide variety of cancers. An increase in the frequency of these chromosomal damage endpoints in a surrogate tissue, such as PBLs, would imply constitutional sensitivity to genetic damage.

This study is, to the inventors' knowledge, the first to validate the use of the CBMN assay, with NNK as the challenge mutagen, in a case-control study by testing the sensitivity of this genomic instability biomarker as a predictor of lung cancer risk. Table 4 shows the predictive probabilities for being a case based on various cutpoints for the numbers of spontaneous and induced MN, NPBs and NBUDs, alone and in combination; as defined by the frequency distribution in control subjects. The probability of being a case increased as the percentile cutpoints increased for all cytogenetic endpoints and the highest probabilities were observed when spontaneous and NNK-induced cytogenetic events were combined. The case-control differences were so striking that we considered, but rejected, alternative explanations. All the cases were enrolled at diagnosis and before initiating treatment; the assays were performed blinded and in batches. We rescored randomly selected samples and obtained high levels of reliability. Further, the values did not differ according to smoking duration or intensity and especially not disease stage (lessening the likelihood that this is a tumor marker, rather than a marker of risk).

From the statistical analyses of the susceptibility studies, a general summary of the results can be arrived at and are summarized below in Table 5. The results shown in Table 5 include the endpoint results for the control population, which in this case was, as noted above, a control population selected to be representative of the population as a whole. Shown are the control mean and control median of endpoints per 1000 cells for each of MN, NPBs and NBUDs, baseline (i.e., spontaneous, not NNK-induced) and NNK-induced. The surprising usefulness and simplicity of the invention can be seen in that the data summarized in Table 5 provides one the ability to now calculate, from any given unknown sample on which an analysis in accordance with the present invention has been performed, a fold increase in risk over the general population for every unit increase over the control median/mean. For example, in the case of MN or NPBs, a subject reporting out a median or mean of about 10 NNK-induced NPBs per 1000 cells will have an about a 225-fold increase in cancer risk, and an individual reporting out about 23 NNK-induced MNs has an approximately 10 fold higher tobacco related cancer risk than does the general population. Similarly, a subject demonstrating an average of 10 NNK-induced NBUDs will have about a 100 fold increase in risk versus the general population, and so on.

TABLE 5

Summary of Susceptibility Results

| | Control Mean | Control Median | Fold increase in risk/unit increase |
|---|---|---|---|
| MN | | | |
| Baseline | 1.98 ± 0.01 | 2 | 2 |
| NNK-induced | 2.62 ± 0.1 | 3 | 2.3 |
| NPBS | | | |
| Baseline | 0.57 ± 0.07 | 0 | 29 |
| NNK-induced | 2.38 ± 0.09 | 2 | 45 |

TABLE 5-continued

Summary of Susceptibility Results

| | Control Mean | Control Median | Fold increase in risk/unit increase |
|---|---|---|---|
| NBUDS | | | |
| Baseline | 0.05 ± 0.02 | 0 | 6 |
| NNK-induced | 0.12 ± 0.03 | 0 | 10 |

In summary, the exemplary study forming the basis of the invention demonstrates differential sensitivity of PBLs from lung cancer patients and healthy controls to NNK-induced genetic damage. The data provide convincing evidence that the CBMN assay is a robust test for detection of this sensitivity and yields results that are a good predictor of lung cancer risk. The simplicity, rapidity, and sensitivity of the CBMN test make it a valuable tool for screening and possibly for prioritizing potential cases for early detection of the disease. This assay appears to give results that yield more accurate predictions than other phenotypic assays also undergoing assessment in this population of lung cancer cases and controls.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents and assay techniques which will achieve useful analytical capabilities may be substituted for the agents and assays described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Hirsch F R, Fischer J R, Niklinski J, Zochbauer-Muller S. Future developments in the treatment of lung cancer. Lung Cancer 2002; 38:S81-S85.
2. Fenech M. Chromosomal biomarkers of genomic instability relevant to cancer. Drug Discov Today 2002; 7:1128-37.
3. Solomon E, Borrow J, Goddard A D. Chromosome aberrations and cancer. Science 1991; 254:1153-60.
4. Hagmar L, Bonassi S, Stromberg U, et al. Chromosomal aberrations in lymphocytes predict human cancer: a report from the European Study Group on Cytogenetic Biomarkers and Health (ESCH). Cancer Res 1998; 58:4117-21.
5. Liou S H, Lung J C, Chen Y H, et al. Increased chromosome-type chromosome aberration frequencies as biomarkers of cancer risk in a blackfoot endemic area. Cancer Res 1999; 59:1481-4.
6. Bonassi S, Hagmar L, Stromberg U, et al. Chromosomal aberrations in lymphocytes predict human cancer independently of exposure to carcinogens. European Study Group on Cytogenetic Biomarkers and Health. Cancer Res 2000; 60:1619-25.

7. Bonassi S, Znaor A, Norppa H, Hagmar L. Chromosomal aberrations and risk of cancer in humans: an epidemiologic perspective. Cytogenet Genome Res 2004; 104:376-82.
8. Smerhovsky Z, Landa K, Rossner P, et al. Risk of cancer in an occupationally exposed cohort with increased level of chromosomal aberrations. Environ Health Perspect 2001; 109:41-5.
9. Tucker J D, Preston R J. Chromosome aberrations, micronuclei, aneuploidy, sister chromatid exchanges, and cancer risk assessment. Mutat Res 1996; 365:147-59.
10. Fenech M. The in vitro micronucleus technique. Mutat Res 2000; 455:81-95.
11. Umegaki K, Fenech M. Cytokinesis-block micronucleus assay in WIL2-NS cells: a sensitive system to detect chromosomal damage induced by reactive oxygen species and activated human neutrophils. Mutagenesis 2000; 15:261-9.
12. Stewenius Y, Gorunova L, Jonson T, Larsson N, Hoglund M, Mandahl N, Mertens F, Mitelman F, Gisselson D. Structural and numerical chromosome changes in colon cancer develop through telomere-mediated anaphase bridges, not through mitotic multipolarity. Proc Natl Acad Sci U S A. 2005,102(15):5541-6.
13. Fenech M, Crott J W. Micronuclei, nucleoplasmic bridges and nuclear buds induced in folic acid deficient human lymphocytes—evidence for breakage-fusion-bridge cycles in the cytokinesis-block micronucleus assay. Mutat Res 2002; 504:131-6.
14. Fenech M. Biomarkers of genetic damage for cancer epidemiology. Toxicology 2002; 181-182:411-6.
15. Serrano-Garcia L, Montero-Montoya R. Micronuclei and chromatid buds are the result of related genotoxic events. Environ Mol Mutagen 2001; 38:38-45.
16. Spitz M R, Wei Q, Dong Q, Amos C I, Wu X. Genetic susceptibility to lung cancer: the role of DNA damage and repair. Cancer Epidemiol Biomarkers Prey 2003; 12:689-98.
17. Thun M J, Lally C A, Flannery J T, Jr. Cigarette smoking and changes in the histopathology of lung cancer. J Natl Cancer Inst 1997; 89:1580-6.
18. Weitberg A B, Corvese D. Oxygen radicals potentiate the genetic toxicity of tobacco-specific nitrosamines. Clin Genet 1993; 43:88-91.
19. Berwick M, Vineis P. Markers of DNA repair and susceptibility to cancer in humans: an epidemiologic review. J Natl Cancer Inst 2000; 92:874-97.
20. Hecht S S. Human urinary carcinogen metabolites: biomarkers for investigating tobacco and cancer. Carcinogenesis 2002; 23:907-22.
21. Cloutier J F, Drouin R, Weinfeld M, O'Connor T R, Castonguay A. Characterization and mapping of DNA damage induced by reactive metabolites of 4-(methylnitrosamino)-1-(3-pyridyl)-1-butanone (NNK) at nucleotide resolution in human genomic DNA. J Mol Biol 2001; 313: 539-57.
22. Fenech M, Morley A A. Measurement of micronuclei in lymphocytes. Mutat Res 1985; 147:29-36.
23. Abdel-Rahman S Z, El Zein R A. The 399Gln polymorphism in the DNA repair gene XRCC1 modulates the genotoxic response induced in human lymphocytes by the tobacco-specific nitrosamine NNK. Cancer Lett 2000; 159:63-71.
24. Hill C E, Affatato A A, Wolfe K J, et al. Gender differences in genetic damage induced by the tobacco-specific nitrosamine NNK and the influence on the Thr241Met polymorphism in the XRCC3 gene. Environ Mol Mutagen 2005; 4:22-9.
25. Affatato A A, Wolfe K J, Lopez M S, Hallberg C, Ammenheuser M M, Abdel-Rahman S Z. Effect of XPD/ERCC2 polymorphisms on chromosome aberration frequencies in smokers and on sensitivity to the mutagenic tobacco-specific nitrosamine NNK. Environ Mol Mutagen 2004; 44:65-73
26. Abdel-Rahman S Z, Salama S A, Au W W, Hamada F A. Role of polymorphic CYP2E1 and CYP2D6 genes in NNK-induced chromosome aberrations in cultured human lymphocytes, Pharmacogenetics 2000; 10:239-49.
27. Fenech M, Chang W P, Kirsch-Volders M, Holland N, Bonassi S, Zeiger E. HUMN project: detailed description of the scoring criteria for the cytokinesis-block micronucleus assay using isolated human lymphocyte cultures. Mutat Res 2003; 534:65-75.
28. Brunnemann K D. Determination of nicotine and minor tobacco alkaloids in indoor air by absorption and gas chromatography. IARC Sci Publ 1993; 109:275-80.
29. Spiegelhalder B, Bartsch H. Tobacco-specific nitrosamines. Eur J Cancer Prey 1996; 5:33-8.
30. Hecht S S, Hoffmann D. The relevance of tobacco-specific nitrosamines to human cancer. Cancer Sury 1989; 8:273-94.
31. Hecht S S, Hoffmann D. Tobacco-specific nitrosamines, and important group of carcinogens in tobacco and tobacco smoke. Carcinogenesis 1988; 9:875-84
32. Adams J D, O'Mara-Adams K J, Hoffmann D. Toxic and carcinogenic agents in undiluted mainstream smoke and sidestream smoke of different types of cigarettes. Carcinogenesis 1987; 8:729-31.
33. Hecht S S. Tobacco smoke carcinogens and lung cancer. J Natl Cancer Inst 1999; 191:1194-210.
34. Padma P R, Amonkar A J, Bhide S V. Mutagenic and cytogenetic studies of N'-nitrosonornicotine and 4-(methylnitrosamino)-1-(3-pyridyl)-1-butanone. Cancer Lett 1989;46:173-80.
35. Cheng T J, Christiani D C, Xu X, Wain J C, Wiencke J H, Kelsey K T. Increased micronucleus frequency in lymphocytes from smokers with lung cancer. Mut Res 1996; 349: 43-50.
36. Bonassi S, Ugolini D, Kirsh-Volders M, Stromberg U, Vermeulen R, Tucker J D. Human population studies with cytogenetic biomarkers: review of the literature and future prospectives. Environ Mol Mutagen 2005; 45:258-70.
37. Fenech M. The cytokinesis-block micronucleus technique and its application to genotoxicity studies in human populations. Environ Health Prespect 1993; 101:101-7.
38. Di Giorgio C, De Meo M P, Laget M, Guiraud H, Botta A, Dumenil G. The micronucleus assay in human lymphocytes: screening for inter-individual variability and application to biomonitoring. Carcinogenesis 1994; 15:313-7.
39. Bonassi S, Neri M, Lando C, et al. Effect of smoking habit on the frequency of micronuclei in human lymphocytes: results from the Human MicroNucleus project. Mutat Res 2003; 543:155-66.
40. Gisselsson D, Bjork J, Hoglund M, et al. Abnormal nuclear shape in solid tumors reflects mitotic instability. Am J Pathol 2001; 158:199-206.
41. El Zein R, Bondy M L, Wang L E, et al. Risk assessment for developing gliomas: a comparison of two cytogenetic approaches. Mutat Res 2001; 490:35-44.
42. Wei Q, Gu J, Cheng L, et al. Benzo(a)pyrene diolepoxide-induced chromosomal aberrations and risk of lung cancer. Cancer Res 1996; 56:3975-9.
43. Spitz M R, Wei Q, Li G, Wu X. Genetic susceptibility to tobacco carcinogenesis. Cancer Invest 1999; 17:645-59.
44. Wu X, Lippman S M, Lee J J. Chromosome instability in lymphocytes: a potential indicator of predisposition to oral premalignant lesions. Cancer Res 2002; 62:2813-8.
45. Schabath M B, Spitz M R, Grossman H B, et al. Genetic instability in bladder cancer assessed by the comet assay. J Natl Cancer Inst 2003; 95:540-7.

46. Hsu T C, Johnston D A, Cherry L M, et al. Sensitivity to genotoxic effects of bleomycin in humans: possible relationship to environmental carcinogenesis. Int J Cancer 1989; 43:403-9.
47. Scott D, Barber J B, Levine E L, Burrill W, Roberts S A. Radiation-induced micronucleus induction in lymphocytes identifies a high frequency of radiosensitive cases among breast cancer patients: a test for predisposition? Br J Cancer 1998; 77:614-20.
48. Rothfuss A, Schutz P, Bochum S, et al. Induced micronucleus frequencies in peripheral lymphocytes as a screening test for carriers of a BRCA1 mutation in breast cancer families. Cancer Res 2000; 60:390-4.
49. Crott J W, Mashiyama S T, Ames B N, Fenech M. The effect of folic acid deficiency and MTHFR C677T polymorphism on chromosome damage in human lymphocytes in vitro. Cancer Epidemiol Biomarkers Prey 2001; 10:1089-96.
50. Kimura M, Umegaki K, Higuschi M, Thomas P, Fenech M. Methylenetetrahydrofolate reductase C677T polymorphism, folic acid and riboflavin are important determinants of genome stability in cultured human lymphocytes. J Nutr 2004; 134(1):48-56.
51. Shi Q, Zhang Z, Li G, et al. Polymorphisms of methionine synthase and methionine synthase reductase and risk of lung cancer: a case-control analysis. Pharmacogenet Genomics 2005; 15:547-55.
52. Offer T, Ho E, Traber M, Bruno R, et al., "A simple assay for frequency of chromosome breaks and loss (micronuclei) by flow cytometry of human lymphocytes," The FASEB Journal, 2005; 19:485-487.
53. Smolewski P, Rion Q, Vellon L et al., "Micronuclei Assay by laser scanning cytometry," Cytometry 2001, 45:19-26.
54. Fimognari C, Sauer-Nehls S et al., "Analysis of radiation induced micronuclei by FISH using a combination of painting and centromeric DNA probes," Mutagenesis 1997; 12:91-5.
55. Matthopoulos D, "Dynamic Analysis of DNA Damage by Flow Cytometry and FISH," The Scientific World Journal, 2006, pages 563-570.
56. Tice R, Agurel E, Anderson D, et al., "Single cell gel/comet assay: Guidelines for in vitro and in vivo genetic toxicology testing," Environmental and Molecular Mutagenesis 2000; 35: 206-221.

The invention claimed is:

1. A method for assessing cancer susceptibility to carcinogens in tobacco smoke in a human subject that has not been diagnosed with lung cancer, comprising the steps of:
   (a) obtaining a sample, wherein the sample comprises nucleated cells obtained from the subject;
   (b) assaying the sample by determining the frequency of chromosomal damage endpoints in the nucleated cells;
   (c) assessing cancer susceptibility to carcinogens in tobacco smoke as a function of the chromosomal damage endpoint frequency.
2. The method of claim 1, wherein the human subject is a known cigarette smoker.
3. The method of claim 1, wherein the subject has a familial history of cancer.
4. The method of claim 1, wherein the sample is a blood sample.
5. The method of claim 1, wherein the chromosomal damage endpoints are selected from the group consisting of micronuclei (MN), nucleoplasmic bridges (NPBs) and nuclear buds (NBUDs).
6. The method of claim 1, wherein determining the frequency of chromosomal damage endpoints comprises determining said frequency in nucleated cells that have not been treated with nitrosamine 4-(methylnitrosamino)-1-(3-pyridyl)-1-butanone (NNK).
7. The method of claim 6, wherein the chromosomal damage endpoints are further defined as spontaneous micronuclei (MN), nucleoplasmic bridges (NPBs) or nuclear buds (NBUDs).
8. The method of claim 1, wherein determining the frequency of chromosomal damage endpoints comprises determining said frequency in nucleated cells that have been treated with nitrosamine 4-(methylnitrosamino)-1-(3-pyridyl)-1-butanone (NNK).
9. The method of claim 8, wherein the chromosomal damage endpoints are further defined as NNK-treated MN, NPBs or NBUDs.
10. The method of claim 5, wherein MNs are quantified by means of the assay.
11. The method of claim 5, wherein NPBs are quantified by means of the assay.
12. The method of claim 5, wherein NBUDs are quantified by means of the assay.
13. The method of claim 5, wherein at least two of MNs, NPBs or NBUDs are quantified by means of the assay.
14. The method of claim 13, wherein all three of MNs, NPBs or NBUDs are quantified by means of the assay.
15. The method of claim 1, wherein determining the frequency of chromosomal damage endpoints comprises subjecting the nucleated cells to a cytokinesis-block micronucleus (CBMN) assay.
16. The method of claim 15, wherein the CBMN assay is automated.
17. The method of claim 1, wherein a selected number of nucleated cells are assayed, and the frequency of chromosomal damage endpoints is determined as a per/cell average of the selected number of cells.
18. The method of claim 17, wherein at least about 500 nucleated cells are assayed.
19. The method of claim 18, wherein at least about 1000 nucleated cells are assayed.
20. The method of claim 1, wherein an increased susceptibility to cancer in the subject is indicated by a higher number of chromosomal damage endpoints as compared to a control number.
21. The method of claim 20, wherein the control number is obtained by conducting the assessment method of steps (a), (b) and (c) on a control population representative of the population as a whole.
22. The method of claim 20, wherein a predicted fold increase in risk is determined.
23. The method of claim 20, wherein a subject who demonstrates an increased susceptibility is placed in a follow-up or screening program.
24. The method of claim 1, wherein the nucleated cells are reticulocytes, buccal cells, bladder wash cells, fibroblasts or lymphocytes.
25. The method of claim 24, wherein the nucleated cells are lymphocytes.
26. The method of claim 25, wherein the lymphocytes are peripheral blood lymphocytes.
27. The method of claim 1, wherein the cancer susceptibility is defined as susceptibility to lung cancer, squamous cell carcinoma of the head and neck or bladder cancer.
28. The method of claim 27, wherein the cancer susceptibility is susceptibility to adenocarcinoma of the lung.

* * * * *

UNITED STATES PATENT AND TRADEMARK OFFICE
CERTIFICATE OF CORRECTION

PATENT NO. : 8,394,592 B2  
APPLICATION NO. : 12/304298  
DATED : March 12, 2013  
INVENTOR(S) : El-Zein et al.

Page 1 of 1

It is certified that error appears in the above-identified patent and that said Letters Patent is hereby corrected as shown below:

In the Specification

In column 1, lines 9-12, delete paragraph and insert --This invention was made with government support under grant numbers CA55769, CA98549, CA70907, DMDD17-02-10707, FAMRI, and NIEHS ES07784 awarded by National Institutes of Health. The Government has certain rights in the invention.--.

Signed and Sealed this  
Twenty-second Day of October, 2013

Teresa Stanek Rea  
*Deputy Director of the United States Patent and Trademark Office*